(12) United States Patent
Shan et al.

(10) Patent No.: US 11,186,809 B1
(45) Date of Patent: Nov. 30, 2021

(54) HIGH-CONCENTRATION ANAEROBIC FERMENTATION APPARATUS

(71) Applicant: Zhejiang University of Science and Technology, Zhejiang (CN)

(72) Inventors: Shengdao Shan, Zhejiang (CN); Tianyong Xiang, Zhejiang (CN); Jingming Li, Zhejiang (CN); Ping Zheng, Zhejiang (CN); Huicai Cheng, Zhejiang (CN); Wu Huang, Zhejiang (CN); Zhirong Wang, Zhejiang (CN); Baolan Hu, Zhejiang (CN); Changai Zhang, Zhejiang (CN)

(73) Assignee: Zhejiang University of Science and Technology, Zhejiang (CN)

( * ) Notice: Subject to any disclaimer, the term of this patent is extended or adjusted under 35 U.S.C. 154(b) by 0 days.

(21) Appl. No.: 17/072,054

(22) Filed: Oct. 16, 2020

(30) Foreign Application Priority Data

Aug. 24, 2020 (CN) .......................... 202010857216.5

(51) Int. Cl.
*C12M 1/107* (2006.01)
*C12M 1/00* (2006.01)
*C12M 1/26* (2006.01)

(52) U.S. Cl.
CPC ............ *C12M 21/04* (2013.01); *C12M 23/34* (2013.01); *C12M 23/36* (2013.01); *C12M 33/14* (2013.01)

(58) Field of Classification Search
CPC ...... C12M 21/04; C12M 23/34; C12M 23/36; C12M 23/02; C12M 33/14; C12M 33/16;
(Continued)

(56) References Cited

U.S. PATENT DOCUMENTS 6,125,736 A * 10/2000 Marin ...................... C12G 1/02
99/276
6,409,461 B1 * 6/2002 Bierschenk ............ B65G 57/32
414/788.2

FOREIGN PATENT DOCUMENTS

CN 201933082 8/2011
CN 105441317 A * 3/2016
(Continued)

OTHER PUBLICATIONS

KR101410722B1—Gun et al. Machine English Translation (Year: 2014).*
(Continued)

*Primary Examiner* — Michael L Hobbs
*Assistant Examiner* — Lenora A Abel
(74) *Attorney, Agent, or Firm* — JCIP Global Inc.

(57) ABSTRACT

A high-concentration anaerobic fermentation apparatus includes a liquid accumulation tank, a fermentation vessel, a feeding assembly, and a biogas residue collecting bin. The feeding assembly includes a hopper and a return conveyor belt including a first portion extending downward from the hopper till below a liquid level, a second portion extending upward from a bottom end of the first portion till above the liquid level, a third portion extending downward from a top end of the second portion till the liquid level, and a fourth portion extending upward from a bottom end of the third portion till out of the liquid level and above the biogas residue collecting bin. A pressure-feed flange is disposed at an outer side of the fermentation vessel, a feed channel is formed between the pressure-feed flange and the first portion, and a discharge channel is formed between the pressure-feed flange and the fourth portion.

20 Claims, 1 Drawing Sheet

(58) Field of Classification Search
CPC ......... C12P 5/023; B01D 53/52; B01D 53/58;
B01D 53/84; B01D 2257/302; B01D
2257/304; B01D 2257/306; B01D
2257/308; B01D 2257/404; B01D
2257/406; B01D 2251/2065; B01D
2251/95; C02F 3/345; C02F 3/34; C02F
1/38; C02F 1/56; C02F 2101/101; C02F
2101/16; C02F 2103/16; C02F 3/08;
C02F 3/087; C02F 3/10; C02F 3/109;
C01B 17/05; C10G 19/02; C10G 29/05;
C10G 1/08; C10G 3/00; C10L 3/102;
C10L 3/10; C05F 5/00; C05F 5/002;
C05F 5/004; C05F 5/006; C05F 5/008;
C05F 7/00; C05F 7/005; C05F 7/02;
C05F 7/04; C05F 9/00; C05F 9/02; C05F
9/04; C05F 17/00; C05F 17/05; C05F
17/10; C05F 17/15; C05F 17/20; C05F
17/30; C05F 17/40; C05F 17/50; C05F
17/939; C05F 17/964; C05F 17/90

USPC ................................ 210/606; 435/290–290.4
See application file for complete search history.

(56) References Cited

FOREIGN PATENT DOCUMENTS

KR            101410722 B1 * 6/2014
KR            101470479 B1 * 12/2014

OTHER PUBLICATIONS

CN 105441317A—Zhizhou et al. Machine English Translation (Year: 2016).*
KR101470479B1—Chang-Soo Machine English Translation (Year: 2013).*

* cited by examiner

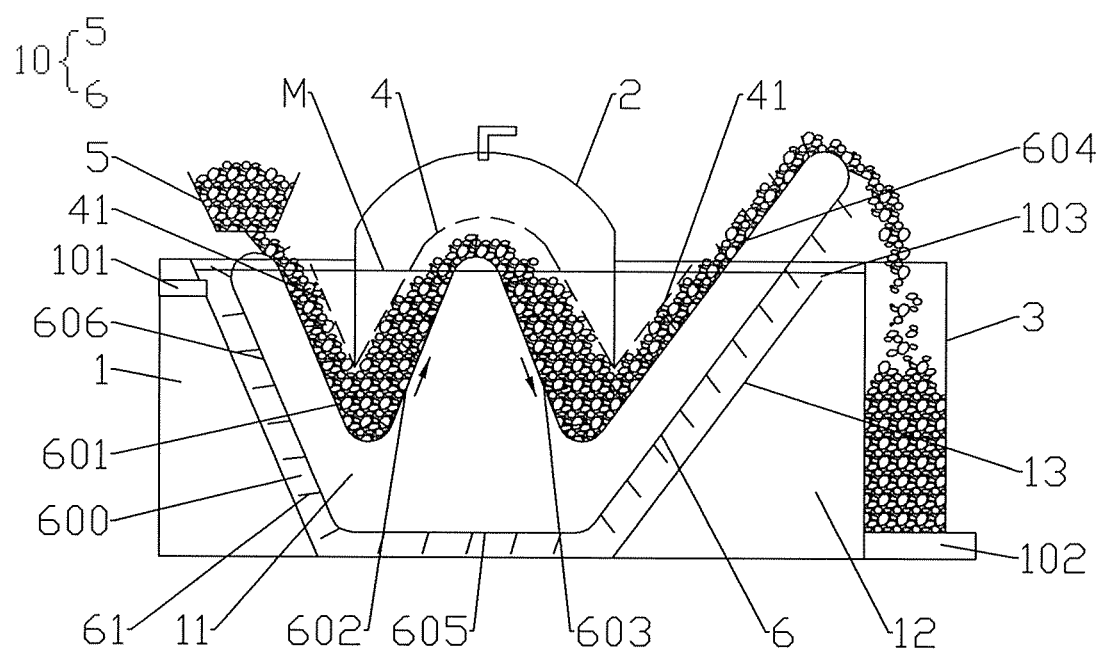

HIGH-CONCENTRATION ANAEROBIC FERMENTATION APPARATUS

CROSS-REFERENCE TO RELATED APPLICATION

This application claims the priority benefit of China application serial no. 202010857216.5, filed on Aug. 24, 2020. The entirety of the above-mentioned patent application is hereby incorporated by reference herein and made a part of this specification.

BACKGROUND

Technical Field

The present disclosure relates to a fermentation apparatus, and more particularly to a high-concentration anaerobic fermentation apparatuses.

Description of Related Art

In some existing anaerobic fermentation apparatuses, e.g., an anaerobic fermentation device for direct biogas production from straw as disclosed in China utility patent publication no. CN201933082U, a stirring member is generally used to stir the solid material such as straw fed into the fermentation chamber so as to adequately mix the solid material with the biogas slurry. Use of the stirring member increases expense. Additionally, in the abovementioned utility patent, discharge of the biogas residue relies on a container that needs be subsequently hoisted out when the biogas slurry reaches a certain amount, which is inconvenient to manipulate.

SUMMARY

The object of the present disclosure is to provide a high-concentration anaerobic fermentation apparatus, which enables adequate mixing of a solid material with biogas slurry during transfer process without a stirring member and realizes automatic discharge.

A high-concentration anaerobic fermentation apparatus includes a liquid accumulation tank, a fermentation vessel, a solid material feeding assembly, and a biogas residue collecting bin. The liquid accumulation tank includes a liquid feedstock inlet port and a biogas slurry outlet port. The fermentation vessel is disposed above the liquid accumulation tank, a bottom end of the fermentation vessel is disposed below a liquid level of the liquid accumulation tank, and the bottom end of the fermentation vessel is open. A porous cover plate is provided in the fermentation vessel, the porous cover plate has a lid shape, a top portion of the porous cover plate is higher than the liquid level of the liquid accumulation tank, and a bottom end of the porous cover plate is connected to the bottom end of the fermentation vessel. The solid material feeding assembly comprises a hopper and a return conveyor belt. The hopper is disposed above the liquid accumulation tank, and the return conveyor belt has grids for receiving the solid material. The return conveyor belt has a first portion extending downward from a lower part of the hopper till below the liquid level of the liquid accumulation tank, a second portion extending upward from a bottom end of the first portion till below the porous cover plate and above the liquid level of the liquid accumulation tank, a third portion extending downward from a top end of the second portion till the liquid level of the liquid accumulation tank, and a fourth portion extending upward from a bottom end of the third portion till out of the liquid level of the accumulation tank and above the biogas residue collecting bin. The first portion, the second portion, the third portion and the fourth portion are successively connected into a W shape. A pressure-feed flange upward warped is disposed at an outer side of the fermentation vessel. A feed channel is formed between the pressure-feed flange and the first portion of the return conveyor belt, and a discharge channel is formed between the pressure-feed flange and the fourth portion of the return conveyor belt.

Further, a partition board is provided in the liquid accumulation tank to partition the liquid accumulation tank into a fermentation chamber and a biogas slurry chamber; the liquid feedstock inlet port is disposed at a top portion of the fermentation chamber and below the liquid level. The fermentation vessel and the solid material feeding assembly are disposed in the fermentation chamber, the top of the partition plate is lower than the liquid level to thereby form a biogas slurry overflow gate which communicates the biogas slurry chamber with the fermentation chamber, and the biogas slurry outlet port is disposed at the bottom of the biogas slurry chamber.

The return conveyor belt further comprises a fifth portion extending along a bottom surface of the fermentation chamber.

Further, the return conveyor belt comprises a sixth portion extending along the sidewall of the fermentation chamber, a top end of the sixth portion is connected to the first portion, and a bottom end of the sixth portion is connected to the fifth portion.

Further, the liquid feedstock inlet port is disposed proximal to the hopper.

Further, the pressure-feed flange is part of the porous cover plate.

Further, a liquid level detector configured for liquid level detection is provided in the fermentation vessel.

Further, a gridded plate is provided on the return conveyor belt, and the gridded plate tilts forward relative to a motion direction of the return conveyor belt.

With the technical solutions above, the present disclosure offers the following advantages. Liquid dung of livestock and poultry is fed into the liquid accumulation tank from the liquid feedstock inlet port. The solid material optionally selects fast rotten or mechanically pulverized straw. The solid material weighed as per a predetermined proportion is fed into the hopper and then transferred under the liquid level via the first portion of the return conveyor belt. The pressure-feed flange is capable of retaining the floating solid material within grids of the return conveyor belt so as to allow the solid material adequately to be mixed with the liquid dung of livestock and poultry in the feed channel, which eliminates provision of a stirring member, thereby solving the problem of unreasonable nutrition structure from single feedstock, facilitating realization of an optimum carbon-nitrogen ratio, and enhancing biogas productivity. The adequately mixed materials are conveyed by the second portion to the fermentation vessel. The porous cover plate cooperates with the gridded structure of the return conveyor belt to retain the floating solid material, which guarantees transfer efficiency of the materials and ensures stable proceeding of mass transfer between the solid-phase material and the liquid-phase material. As the top end of the second portion is higher than the liquid level of the liquid accumulation tank, during the rotary process of the return conveyor belt, the floating solid material is collectible in the grids and conveyed out by the third portion and the fourth portion; in this way, encrustation in the fermentation vessel is overcome while the liquid feedstock is agitated. The top end of the fourth portion is higher than the liquid level of the liquid accumulation tank, which enables solid-liquid separation during the material transferring process, thereby facilitating subsequent processing of the fermented residue. The fermented residue drops down from the top of the fourth portion smoothly into the biogas residue collecting bin, thereby realizing automated discharge. The gridded structure of the return conveyor belt enables stable conveying of the solid material below the liquid level, which solves common problems such as material blockage and sediment during the high-concentration anaerobic fermentation process and also overcomes encrustation in the fermentation vessel, etc., and is thus applicable for high-concentration anaerobic fermentation.

BRIEF DESCRIPTION OF THE DRAWINGS

Hereinafter, the present disclosure will be further illustrated with reference to the accompanying drawings.

FIGURE is a structural schematic diagram of a high-concentration anaerobic fermentation apparatus.

DESCRIPTION OF THE EMBODIMENTS

As shown in FIGURE, embodiments of the present disclosure provide a high-concentration anaerobic fermentation apparatus including a liquid accumulation tank 1, a fermentation vessel 2, a solid material feeding assembly, and a biogas residue collecting bin 3. The liquid accumulation tank 1 includes a liquid feedstock inlet port 101 and a biogas slurry outlet port 102. The fermentation vessel 2 is disposed above the liquid accumulation tank 1, a bottom end of the fermentation vessel 2 is disposed lower than a liquid level of the liquid accumulation tank 1, and the bottom end of the fermentation vessel 2 is open. A porous cover plate 4 is provided in the fermentation vessel 2, the porous cover plate 4 has a lid shape, a top end of the porous cover plate 4 is higher than the liquid level (M) of the liquid accumulation tank 1, and a bottom end of the porous cover plate 4 is connected to the bottom end of the fermentation vessel 2. The solid material feeding assembly comprises a hopper 5 and a return conveyor belt 6. The hopper 5 is disposed above the liquid accumulation tank 1, and the return conveyor belt 6 has grids 600 for receiving solid materials. The return conveyor belt 6 has a first portion 601 extending downward from a lower part of the hopper 5 till below the liquid level of the liquid accumulation tank 1, a second portion 602 extending upward from a bottom end of the first portion 601 till below the porous cover plate 4 and above the liquid level of the liquid accumulation tank 1, a third portion 603 extending downward from a top end of the second portion 602 till the liquid level of the liquid accumulation tank 1, and a fourth portion 604 extending upward from a bottom end of the third portion 603 till out of the liquid level of the liquid accumulation tank 1 and above the biogas residue collecting bin 3. The first portion 601, the second portion 602, the third portion 603 and the fourth portion 604 are successively connected into a W shape. A pressure-feed flange 41 warped upward is disposed at an outer side of the fermentation vessel 2. A feed channel is formed between the pressure-feed flange 41 and the first portion 601 of the return conveyor belt 6, and a discharge channel is formed between the pressure-feed flange 41 and the fourth portion 604 of the return conveyor belt 6.

Liquid dung of livestock and poultry is fed into the liquid accumulation tank 1 from the liquid feedstock inlet port 101. The solid material optionally selects fast rotten or mechanically pulverized straw. The solid material weighed as per a predetermined proportion is fed into the hopper 5 and then conveyed under the liquid level via the first portion 601 of the return conveyor belt 6. The pressure-feed flange 41 is capable of limiting the floating solid materials within the grids 600 of the return conveyor belt 6, so as to allow the solid material adequately to be mixed with the liquid dung of livestock and poultry in the feed channel, which eliminates provision of a stirring member, thereby solving the problem of unreasonable nutrition structure from a single raw material, facilitating realization of an optimum carbon-nitrogen ratio, and enhancing biogas productivity. The adequately mixed material is conveyed by the second portion 602 to the fermentation vessel 2. The porous cover plate 4 cooperates with the structure of grids 600 of the return conveyor belt 6 to limit the position of the floating solid material, which guarantees the transfer efficiency of the materials and ensures stable proceeding of mass transfer between the solid-phase material and the liquid-phase material. As the top end of the second portion 602 is higher than the liquid level of the liquid accumulation tank 1, during the turning-around process of the return conveyor belt 6, the solid material is collectible in the grids 600 and conveyed out by the third portion 603 and the fourth portion 604. In this way, encrustation in the fermentation vessel 2 is overcome while the liquid feedstock is agitated. The top end of the fourth portion 604 is higher than the liquid level of the liquid accumulation tank 1, which enables solid-liquid separation during the material transferring process, thereby facilitating subsequent processing of the fermented residue. The fermented residue drops down from the top end of the fourth portion smoothly into the biogas residue collecting bin 3, thereby realizing automated discharge. The structure of the grids 600 of the return conveyor belt 6 enables stable transfer of the solid material below the liquid level, which solves common problems such as material blockage and sediment during the high-concentration anaerobic fermentation process and encrustation in the fermentation vessel 2, etc., and is thus applicable for high-concentration anaerobic fermentation.

To facilitate collection of fermented biogas slurry, a partition board 13 is optionally provided in the liquid accumulation tank 1 to partition the liquid accumulation tank 1 into a fermentation chamber 11 and a biogas slurry chamber 12. The liquid feedstock inlet port 101 is disposed at a top portion of the fermentation chamber 11 and below the liquid level, and the fermentation vessel 2 and the solid material feeding assembly is disposed in the fermentation chamber 11, a top end of the partition board 13 is below the liquid level to thereby form a biogas slurry overflow gate 103 which communicates the biogas slurry chamber 12 with the fermentation chamber 11, and the biogas slurry outlet port 102 is disposed at the bottom end of the biogas slurry chamber 12. The overflow via the biogas slurry overflow gate 103 provides overload protection to the fermentation chamber 2.

After long-time use, sludge is easily deposited on a bottom surface of the fermentation chamber 11. In this embodiment, the return conveyor belt 6 realizes automatic sludge cleaning. Specifically, the return conveyor belt 6 further comprises a fifth portion 605 extending along the bottom surface of the fermentation chamber 11. When the fifth portion 605 moves along the bottom surface of the fermentation chamber 11, the fifth portion 605 scrapes up the deposited sludge. The sludge moves to the top end of the first portion 601 with the grids 600. As the sludge is rich of anaerobic microorganisms, the sludge mixing with the solid material enhances fermentation effect. Finally, the sludge is separated from the return conveyor belt 6 at the top end of the fourth portion 604 and falls into the biogas residue collecting bin 3, thereby realizing automatic cleaning of the sludge.

To bring more sludge to the top end of the first portion 60, the return conveyor belt 6 further comprises a sixth portion 606 extending along the sidewall of the fermentation chamber 11. A top end of the sixth portion 606 is connected to the first portion 601, and a bottom end of the sixth portion 606 is connected to the fifth portion 605. The sixth portion 606 moves along the sidewall of the fermentation chamber 11, such that most of the sludge is retained within the grids 600.

To mix the unfermented liquid dung of livestock and poultry, the liquid feedstock inlet port 101 is optionally disposed proximal to the hopper 5.

In this embodiment, the pressure-feed flange 41 is part of the porous cover plate 4, i.e., the pressure-feed flange 41 is manufactured simultaneously with the porous cover plate 4. It may be understood that the pressure-feed flange 41 may be part of the fermentation vessel 2.

To realize automated and optimized control, a liquid level detector configured for liquid level detection is optionally provided in the fermentation vessel 2. Fermentation effect is enhanced by controlling motion of the return conveyor belt 6 based on the detected liquid level and the fermentation time.

A gridded plate 61 is provided on the return conveyor belt 6. A motion direction of the gridded plate 61 relative to the return conveyor belt 6 tilts forward, which achieves an improved retaining effect. For example, at the first portion 601, the gridded plate 61 tilts downward, this facilitates pressing of the solid material downward and conveying it below the liquid level. At the third portion 603, the same effect is also achieved. While at the fourth portion 604, the gridded plate 61 tilts upward, this facilitates solid-liquid separation, limiting the fermented residue from flowing back to the fermentation chamber 11 along with the biogas slurry. After the return conveyor belt 6 passes through the top end of the fourth portion 604 and starts moving downward, the gridded plate 61 turns to tilt downward, which facilitates separation of the fermented residue in the grids 600 from the grids 600 faster. The return conveyor belt 6 is optionally driven by a traction motor disposed at the top end of the fourth portion. In an embodiment, the turning-around direction of the return conveyor belt 6 refers to the direction indicated by the arrow in FIGURE.

In the present disclosure, the return conveyor belt 6 is an integral piece. The first portion 601, the second portion 602, the third portion 603, the fourth portion 604, the fifth portion 605 and the sixth portion 606, as mentioned above, are only intended for clearly describing the motion path of the return conveyor belt 6. During the turning-around process, the return conveyor belt 6 motions continuously, i.e., any portion of the return conveyor belt 6 will move to the first portion 601, the second portion 602, the third portion 603, the fourth portion 604, the fifth portion 605 and the sixth portion 606.

Besides the embodiments illustrated above, the present disclosure also has other embodiments. Those skilled in the art may make various variations and alternations based on the present disclosure, and such variations and alterations shall fall within the scope defined by the appended claims without departing from the spirit of the present disclosure.

What is claimed is:

1. A high-concentration anaerobic fermentation apparatus, comprising:
    a liquid accumulation tank;
    a fermentation vessel, independent from the liquid accumulation tank, wherein a lower portion of the fermentation vessel is located inside the liquid accumulation tank;
    a solid material feeding assembly, including a hopper and a return conveyor belt directly connected to a lower part of the hopper, wherein the hopper is disposed above the liquid accumulation tank, solid material is fed into the hopper, and the return conveyor belt has grids for receiving the solid material; and
    a biogas residue collecting bin;
    wherein the liquid accumulation tank includes a liquid feedstock inlet port and a biogas slurry outlet port;
    the fermentation vessel is disposed above the liquid accumulation tank, a bottom end of the fermentation vessel is disposed below a liquid level of the liquid accumulation tank, and the bottom end of the fermentation vessel is open;
    a porous cover plate includes a main body and a pressure-feed flange, the main body is dome-shaped and is disposed inside the fermentation vessel, the pressure-feed flange is warped upward from a bottom end of the main body and extends outside the fermentation vessel, a top portion of the main body of the porous cover plate is higher than the liquid level of the liquid accumulation tank, the bottom end of the main body of the porous cover plate is directly connected to the bottom end of the fermentation vessel;
    the return conveyor belt has:
        a first portion extending downward from the lower part of the hopper till below the liquid level of the liquid accumulation tank;
        a second portion extending upward from a bottom end of the first portion till below the porous cover plate and above the liquid level of the liquid accumulation tank, wherein a top end of the second portion is higher than the liquid level;
        a third portion extending downward from a top end of the second portion till below the liquid level of the liquid accumulation tank, wherein the second portion and the third portion correspond in position with the fermentation vessel; and
        a fourth portion extending upward from a bottom end of the third portion till out of the liquid level of the accumulation tank and above the biogas residue collecting bin, wherein a top end of the fourth portion is higher than the liquid level, and the first portion, the second portion, the third portion and the fourth portion are successively connected into a W shape;
    a feed channel is formed between the pressure-feed flange and the first portion of the return conveyor belt, a discharge channel is formed between the pressure-feed flange and the fourth portion of the return conveyor belt, the solid material in the hopper is transferred under the liquid level via the feed channel, the pressure-feed flange limits the solid material within the grids to allow the solid material to be mixed with liquid in the feed channel, and the solid material being mixed is conveyed by the second portion to the fermentation vessel; the porous cover plate cooperates with the grids to limit the solid material being floated, and the solid material is collected in the grids and conveyed out of the discharge channel to the biogas residue collecting bin.

2. The high-concentration anaerobic fermentation apparatus according to claim 1, wherein a partition board is provided in the liquid accumulation tank to partition the liquid accumulation tank into a fermentation chamber and a biogas slurry chamber; the liquid feedstock inlet port is disposed at a top portion of the fermentation chamber and below the liquid level; the fermentation vessel and the solid material feeding assembly are disposed in the fermentation chamber, a top end of the partition board is lower than the liquid level to form a biogas slurry overflow gate which communicates the biogas slurry chamber with the fermentation chamber, and the biogas slurry outlet port is disposed at a bottom portion of the biogas slurry chamber.

3. The high-concentration anaerobic fermentation apparatus according to claim 2, wherein the return conveyor belt further comprises a fifth portion extending along a bottom surface of the fermentation chamber.

4. The high-concentration anaerobic fermentation apparatus according to claim 3, wherein the return conveyor belt further comprises a sixth portion extending along a sidewall of the fermentation chamber, a top end of the sixth portion is connected to the first portion, and a bottom end of the sixth portion is connected to the fifth portion.

5. The high-concentration anaerobic fermentation apparatus according to claim 1, wherein the liquid feedstock inlet port is disposed proximal to the hopper.

6. The high-concentration anaerobic fermentation apparatus according to claim 1, wherein the pressure-feed flange is part of the porous cover plate.

7. The high-concentration anaerobic fermentation apparatus according to claim 1, wherein a liquid level detector configured for liquid level detection is provided in the fermentation vessel.

8. The high-concentration anaerobic fermentation apparatus according to claim 1, wherein a gridded plate forming the grids is provided on the return conveyor belt, and the gridded plate tilts forward relative to a motion direction of the return conveyor belt.

9. The high-concentration anaerobic fermentation apparatus according to claim 2, wherein the liquid feedstock inlet port is disposed proximal to the hopper.

10. The high-concentration anaerobic fermentation apparatus according to claim 2, wherein the pressure-feed flange is part of the porous cover plate.

11. The high-concentration anaerobic fermentation apparatus according to claim 2, wherein a liquid level detector configured for liquid level detection is provided in the fermentation vessel.

12. The high-concentration anaerobic fermentation apparatus according to claim 2, wherein a gridded plate forming the grids is provided on the return conveyor belt, and the gridded plate tilts forward relative to a motion direction of the return conveyor belt.

13. The high-concentration anaerobic fermentation apparatus according to claim 3, wherein the liquid feedstock inlet port is disposed proximal to the hopper.

14. The high-concentration anaerobic fermentation apparatus according to claim 3, wherein the pressure-feed flange is part of the porous cover plate.

15. The high-concentration anaerobic fermentation apparatus according to claim 3, wherein a liquid level detector configured for liquid level detection is provided in the fermentation vessel.

16. The high-concentration anaerobic fermentation apparatus according to claim 3, wherein a gridded plate forming the grids is provided on the return conveyor belt, and the gridded plate tilts forward relative to a motion direction of the return conveyor belt.

17. The high-concentration anaerobic fermentation apparatus according to claim 4, wherein the liquid feedstock inlet port is disposed proximal to the hopper.

18. The high-concentration anaerobic fermentation apparatus according to claim 4, wherein the pressure-feed flange is part of the porous cover plate.

19. The high-concentration anaerobic fermentation apparatus according to claim 4, wherein a liquid level detector configured for liquid level detection is provided in the fermentation vessel.

20. The high-concentration anaerobic fermentation apparatus according to claim 4, wherein a gridded plate forming the grids is provided on the return conveyor belt, and the gridded plate tilts forward relative to a motion direction of the return conveyor belt.

* * * * *